United States Patent
Schöb (10) Patent No.: US 6,676,383 B2
(45) Date of Patent: Jan. 13, 2004

(54) METHOD AND A PUMP APPARATUS FOR THE GENERATION OF AN ADJUSTABLE, SUBSTANTIALLY CONSTANT VOLUME FLOW OF A FLUID AND A USE OF THIS METHOD

(75) Inventor: Reto Schöb, Volketswil (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 10/218,257

(22) Filed: Aug. 9, 2002

(65) Prior Publication Data

US 2003/0035730 A1 Feb. 20, 2003

(30) Foreign Application Priority Data

Aug. 16, 2001 (EP) .............................. 01810790

(51) Int. Cl.⁷ .................... F04B 17/00; F16L 55/04
(52) U.S. Cl. .................... 417/53; 415/1; 138/26
(58) Field of Search ................ 415/1; 417/53, 417/423.1; 138/26

(56) References Cited

U.S. PATENT DOCUMENTS

| 5,307,288 A | 4/1994 | Haines |
| 5,563,490 A | * 10/1996 | Kawaguchi et al. ........ 318/808 |
| 5,785,681 A | * 7/1998 | Indravudh .................... 604/65 |
| 6,149,508 A | 11/2000 | Vanell et al. |
| 6,227,797 B1 | * 5/2001 | Watterson et al. .......... 415/107 |
| 6,241,485 B1 | 6/2001 | Warwick |
| 6,250,880 B1 | * 6/2001 | Woodard et al. |
| 2002/0192072 A1 | * 12/2002 | Kardasz et al. ............. 415/127 |

FOREIGN PATENT DOCUMENTS

| DE | 42 43 118 A1 | 6/1994 |
| JP | 09 137792 | 5/1997 |

* cited by examiner

Primary Examiner—Charles G. Freay
(74) Attorney, Agent, or Firm—Townsend and Townsend and Crew LLP (57) ABSTRACT

A method and a pump apparatus are provided for the generation of an adjustable, substantially constant volume flow of a fluid by means of a pump apparatus, wherein the fluid (5) is forwarded by the pump apparatus (1) from a reservoir (2) into a flow connection (4). A rotary pump (1) is used as the pump apparatus and the rotary pump (1) is operated at an efficiency which is less than half the maximum efficiency ($\eta_{max}$) of the rotary pump (1).

21 Claims, 7 Drawing Sheets

METHOD AND A PUMP APPARATUS FOR THE GENERATION OF AN ADJUSTABLE, SUBSTANTIALLY CONSTANT VOLUME FLOW OF A FLUID AND A USE OF THIS METHOD

BACKGROUND OF THE INVENTION

The invention relates to a method and a pump apparatus for the generation of an adjustable, substantially constant volume flow of a fluid and to the use of this method.

The necessity exists of transporting a fluid in a metered manner in many industrial processes and in the conduct of numerous methods; i.e. a substantially constant volume flow of the fluid should be forwarded in the sense that the quantity of fluid forwarded per unit of time is constant. An example which can be given here is chemical-mechanical polishing (CMP) processes such as are used in the semi-conductor industry. In such processes, a suspension, which is usually called a slurry and is typically made up of very fine solid particles and a liquid, is brought onto a rotating wafer and serves there for the polishing or lapping of the very fine semi-conductor structures. In this respect, it is necessary for the suspension (slurry) to be applied to the wafer surface with a constant, adjustable volume flow, i.e. in a metered manner.

In other processes, for example the application of photosensitive resist onto the wafer, it is necessary to transport a metered quantity of fluid, which can as a rule be realized by the transportation of a constant volume flow over a predetermined time.

Volumetric pumps such as peristaltic pumps, gear pumps, piston pumps and diaphragm pumps are used nowadays for such metered forwarding. Such volumetric pumps have the characteristic that they forward a well-defined quantity of fluid per working cycle. With a piston pump, for example, the fluid volume forwarded per stroke is fixed by the piston area and the piston stroke. A constant volume flow can thus be generated because the same volume of fluid is forwarded with each stroke of the piston.

Volumetric pumps, however, have characteristics which can prove to be disadvantageous in some applications, for example they generally generate pulsating fluid flows. The pressure fluctuations associated with this can prove to be very disturbing. They can also facilitate deposits or agglomeration of particles. Moreover, with special liquids, such as with the already mentioned slurry suspensions, the solid particles can result in substantial damage to the pump due to abrasion, in particular to the sealing components between the suction side and the pressure side. For instance, leaks can occur due to the abrasive particles, for example, along the piston in a piston pump, as the piston rings and/or the cylinder wall are damaged.

SUMMARY OF THE INVENTION

It is an object of the invention to provide another method and an apparatus with which an adjustable, substantially constant volume flow of a fluid can be generated. The method should be capable of being realized as simply as possible apparatus-wise and also, in particular, be suitable for the transportation of suspensions, for example slurry.

In accordance with the invention, a method is provided for the generation of an adjustable, substantially constant volume flow of a fluid by means of a pump apparatus, in which method the fluid is forwarded by the pump apparatus from a reservoir into a flow connection. A rotary pump is used as the pump apparatus and the rotary pump is operated at an efficiency which is less than half of the maximum efficiency of the rotary pump. The rotary pump is preferably operated at at most twenty percent of its maximum efficiency.

Of importance for the invention is the recognition that with such operating states of the rotary pump, which correspond to a very low efficiency, there is a unique relationship between the speed of rotation of the pump, more specifically the speed of rotation of the pump rotor, and the volume flow forwarded by the pump. A constant volume flow of the fluid can thus be set in this operating range directly via the speed of rotation of the pump rotor without sensors being necessary for the detection of the volume flow or control circuits for the rotary pump. For this reason, the method of the invention can be realized very easily apparatus-wise. The desired volume flow is simply controlled and adjusted via the speed of rotation of the rotary pump.

The volume flow generated by the rotary pump is free of pulsations as a result of the operating principle of a rotary pump, whereby the risk of unwanted deposits is also substantially reduced.

Furthermore, with a rotary pump, the inlet is in constant flow communication with the outlet of the pump. There are no diaphragms, pistons or similar components which can seal off the outlet with respect to the inlet. This reduces the risk of damage to the pump when forwarding abrasive particles.

Moreover, a rotary pump can also work with a closed outlet, that is, with a forwarded volume flow of zero, without incurring damage. The possibility thereby exists to restrict the constant volume flow time-wise or to interrupt it by an ON/OFF valve downstream of the pump. Consequently, with the method of the invention, the metered dispensing of a predetermined quantity of fluid is also possible without complex control mechanisms being required for the forwarding performance of the pump.

It is particularly advantageous if the fluid is forwarded to a dispensing apparatus through the flow connection, with the total flow resistance of the flow connection and of the dispensing apparatus being selected such that its mean value is substantially larger than the fluctuations of the flow resistance during operation—that is, at least twice as large. Then, namely, the flow resistance of the dispensing apparatus (load resistance) can, for example, vary without the flow—that is, the volume flow forwarded by the pump—changing.

The method of operating a rotary pump with an efficiency which is less than half the maximum efficiency of the rotary pump can also be advantageously used to determine the viscosity, and in particular the dynamic viscosity, of a fluid. This application of the rotary pump is independent of whether the pump is used for the generation of a constant volume flow or not.

The method of the invention can preferably be used for the forwarding of suspensions, in particular for the forwarding of slurry, especially in a CMP process.

The pump apparatus of the invention is characterized in that it is designed as a rotary pump.

The invention will be explained in more detail in the following apparatus-wise and technically method-wise by way of embodiments and with reference to the drawing.

DESCRIPTION OF THE PREFERRED EMBODIMENTS

The method of the invention for the generation of an adjustable, substantially constant volume flow of a fluid is characterized in particular in that a rotary pump is used and operated at an efficiency which is less than half the maximum efficiency of the rotary pump. It preferably amounts to at most twenty percent of the maximum efficiency.

Figure 4:
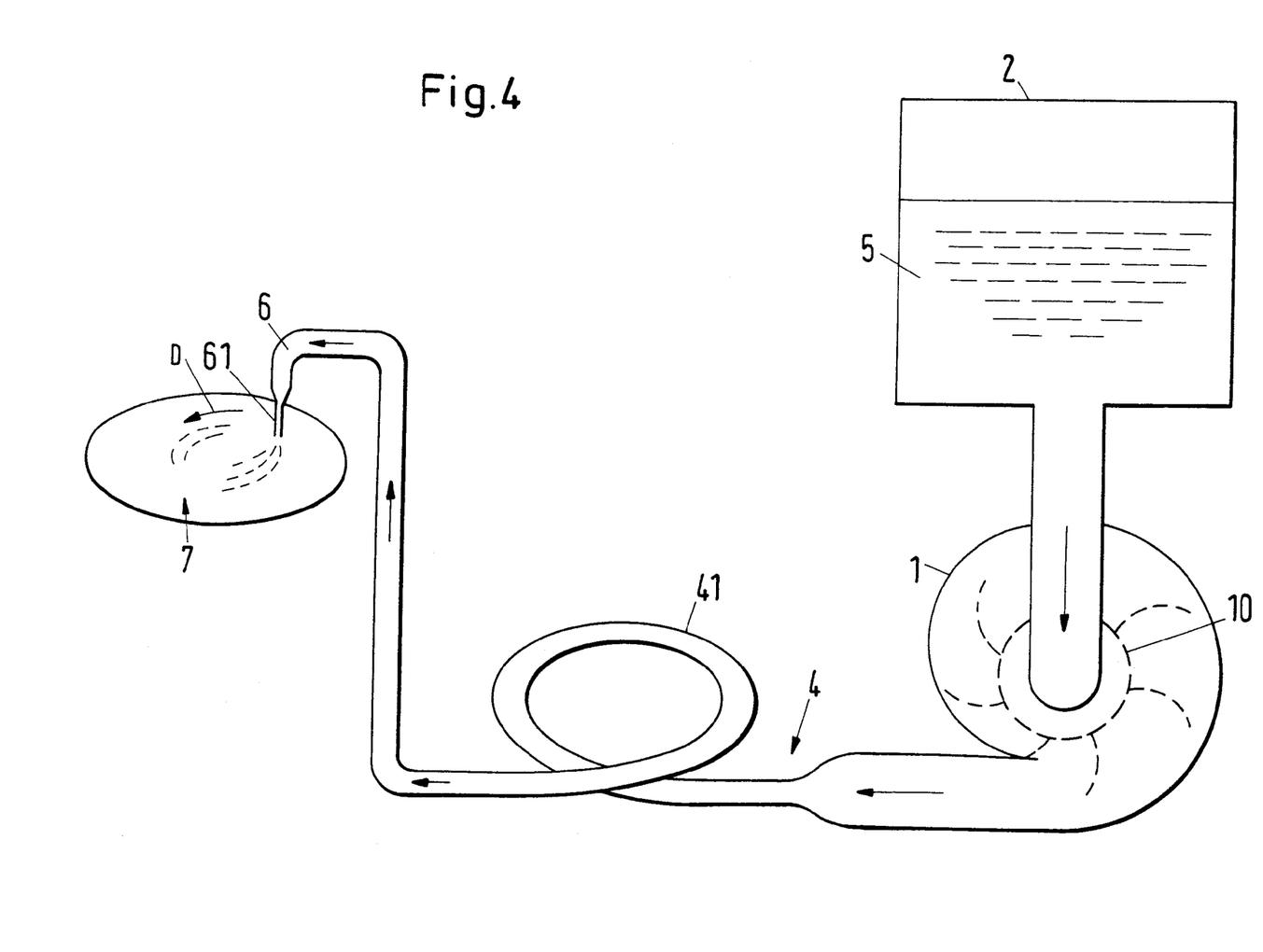
FIG. 4 is a schematic illustration of an arrangement for carrying out an embodiment of the method of the invention.

FIG. 4 shows an arrangement to carry out an embodiment of the method of the invention in a schematic illustration. The inlet of a rotary pump 1, which is here designed as a centrifugal pump and has a rotor 10, is connected to a reservoir 2 in which the fluid 5 to be forwarded is located. The outlet of the rotary pump 1 is connected via a flow connection 4 to a dispensing apparatus 6 which is here provided with a nozzle 61.

Reference is made in the following, by way of example, to a particularly important use in practice, namely that the method of the invention is used as part of a chemical-mechanical polishing process (CMP) in the semi-conductor industry. In these processes, a suspension (known as a slurry) of fine solid particles in a liquid is applied to a rotating wafer 7 and there serves for the lapping or polishing of the very fine semi-conductor structures. The rotation of the wafer 7 is indicated by the arrow D in FIG. 4. The fluid to be forwarded in this example is the suspension called slurry.

Rotary pumps, also known as centrifugal pumps, include all those pump apparatuses which have a rotor or an impeller wheel by whose rotation a momentum transfer to the fluid to be forwarded takes place. The term rotary pump in particular includes centrifugal pumps, axial pumps and side channel pumps. With a rotary pump, the inlet and the outlet are typically in constant flow communication. There are therefore, for example, no diaphragms between the inlet and the outlet.

The rotary pump preferably has a fully magnetically supported rotor in particular for such fluids which contain solid particles or which are of high purity. The absence of mechanical bearings for the rotor has several advantages. For instance, the problem is avoided that abrasive particles can damage mechanical bearings. Furthermore, there is no risk of contamination of the fluid by lubricants or bearing abrasion.

A particularly preferred rotary pump is disclosed for example in EP-A-0 819 330 or U.S. Pat. No. 6,100,618. This rotary pump has a so-called integral rotor 10 and is designed as a bearing-free motor. The term integral rotor means in this respect that the pump rotor and the rotor of the motor driving the pump are identical. The rotor works both as a rotor of the motor drive and as a rotor of the pump. The term bearing-free motor means that the rotor is completely magnetically supported, with no separate magnetic bearings being provided. The stator is both the stator of the electric drive and the stator of the magnetic support and includes a drive winding of the pole pair number p and a control winding of the pole pair number p ±1. It is thus possible to both drive the motor and to support it magnetically completely free of contact in the stator. Reference is made here to the already cited documents with respect to further details of such a rotary pump.

The term efficiency within the framework of these statements means the hydraulic efficiency of the rotary pump, that is, the ratio of hydraulic performance (forwarding performance) of the pump and the mechanical performance for the drive of the rotor (without any optionally present friction losses in bearings or the like).

Figure 1:
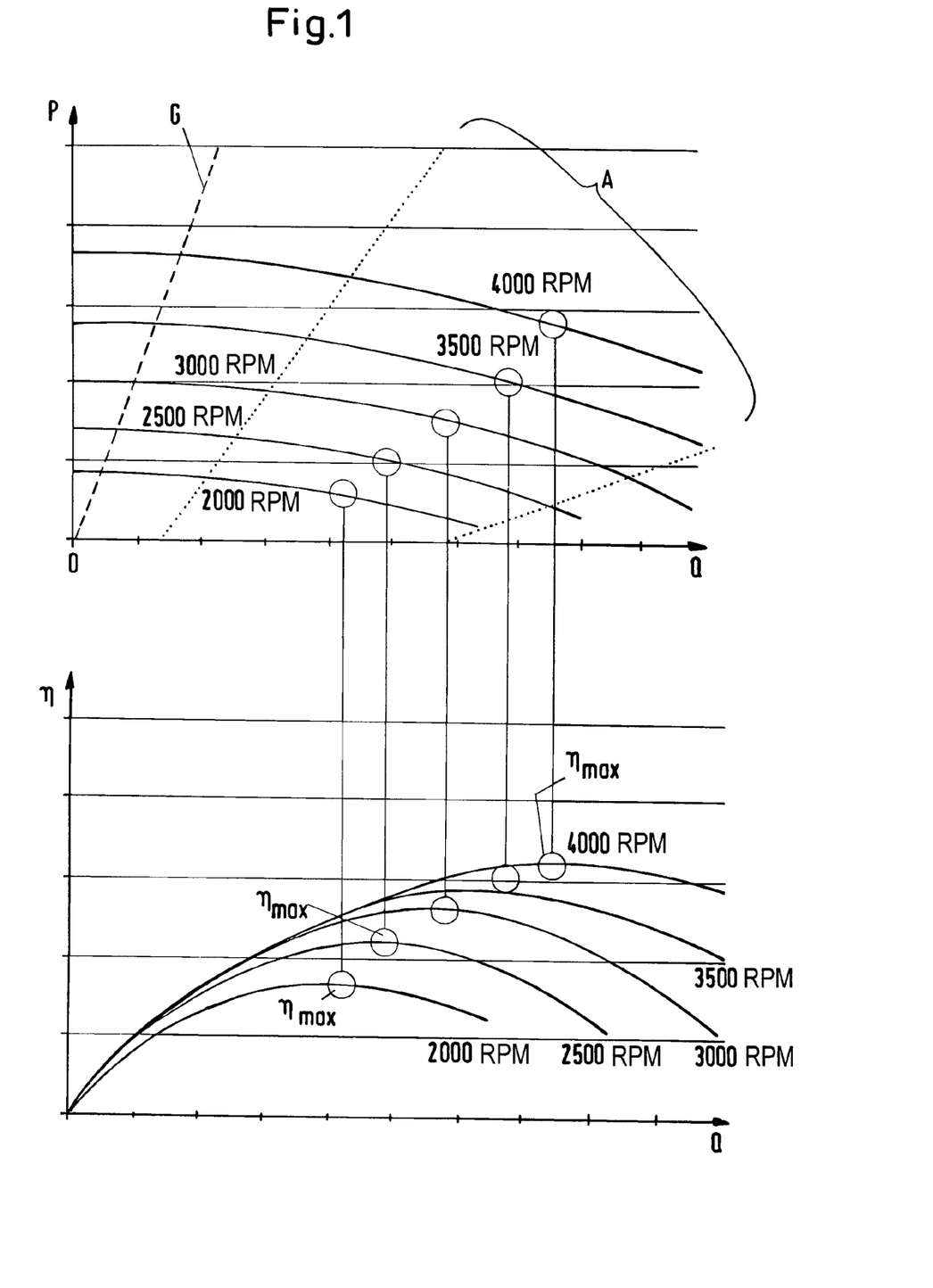
FIG. 1 is an illustration of the relationship between pressure (top) or efficiency (bottom) and throughflow in a rotary pump.

FIG. 1 shows in its upper part an illustration of the relationship between the pressure p (ordinate) and the throughflow or volume flow Q (abscissa) such as is typical for a rotary pump 1 known per se. The different curves, which are termed pressure throughflow characteristics or restrictor curves of the rotary pump 1, correspond to different speeds of rotation $\omega$ of the pump such as are given in revolutions per minute (U/RPM) in FIG. 1. The efficiency $\eta$ is entered on the ordinate with the same abscissa in the lower part of FIG. 1. It can be seen that a maximum efficiency $\eta_{max}$ exists for each speed of rotation $\omega$ of the rotary pump. The position of the maximum is in this respect dependent on the speed of rotation and is indicated in each case in FIG. 1 (bottom) by a circle.

Rotary pumps, in particular centrifugal pumps, are normally used where high pump quantities are important, that is, a maximization of the transportation performance. For this reason, such pumps are operated in the range in which the hydraulic efficiency is maximum. This range is designated by A at the top of FIG. 1 and is bounded by the two dotted straight lines. In this operating range, it is not possible to determine the throughflow sufficiently accurately without appropriate measurements being made with suitable sensors.

The recognition that a unique relationship exists between the speed of rotation of the pump rotor and the forwarded volume flow for those operating ranges of the rotary pump 1 in which the efficiency is well below the maximum efficiency is important for the method of the invention. In these operating ranges, which are to the left of the straight lines G drawn in dashed form in FIG. 1 (top), the rotary pump 1 can be used in a simple manner as a metering pump to generate an adjustable, substantially constant volume flow without complex controls of the quantity forwarded or the associated sensors being required for this.

Since a unique relationship between the speed of rotation of the rotary pump 1 and the volume flow (flow) of the fluid exists at these operating states with a very low efficiency, the volume flow forwarded by the rotary pump can be set directly to the desired value via a control of the speed of rotation. The rotary pump can thus be used as a metering pump.

Figure 2:
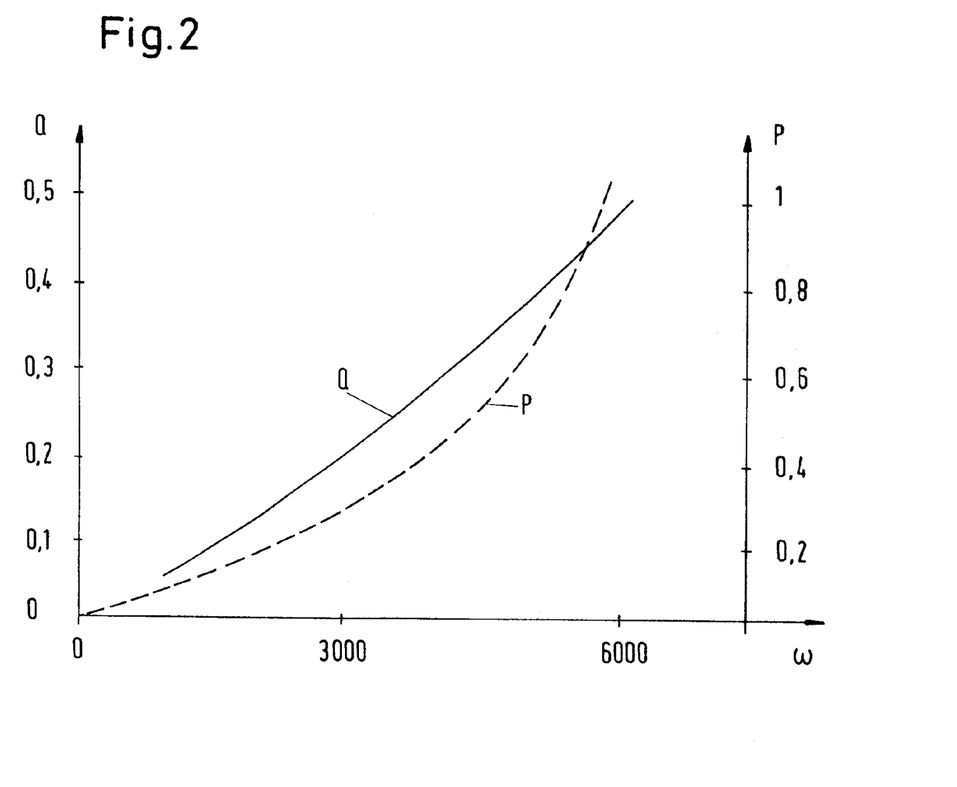
FIG. 2 is an illustration of the relationship between throughflow (solid lines) or pressure (broken lines) and speed of rotation for an embodiment of the method of the invention.

The unique relationship between the throughflow (volume flow) Q and the speed of rotation $\omega$ of the rotary pump for such an operating range in which the rotary pump works at a very low efficiency is illustrated in FIG. 2. The dependence of the throughflow Q on the speed of rotation $\omega$ is illustrated by the solid line in FIG. 2. The dependence of the pressure p, more precisely of the pumping head, on the speed of rotation $\omega$ is likewise drawn in in FIG. 2 by means of the dashed line. A unique relationship also exists between these two parameters.

Both dependences shown in FIG. 2 are as a rule not linear, but can be determined in a calibration measurement. The volume flow of the fluid to be forwarded is preferably only adjusted by the speed of rotation of the rotary pump. For this purpose, a calibration measurement is made beforehand in order to determine the throughflow/speed of rotation curve illustrated as a solid line in FIG. 2. This curve can then be stored as a mathematical function, for example a polynomial approximation, or as an electronic look-up table, in a memory. The associated speed of rotation for the desired, substantially constant volume flow is then looked up in the look-up table during the operation of the rotary pump. The desired constant volume flow can then be realized by setting the corresponding speed of rotation.

The clear relationship between the speed of rotation and the volume flow depends on the fluid to be forwarded, in particular on its viscosity, which is known to be a measure for the internal friction in the fluid. Operating the rotary pump in such operating ranges in which it works at a very low efficiency, preferably at at most twenty percent of its maximum efficiency $\eta_{max}$, allows the viscosity of the fluid to be forwarded to be determined in a simple manner. This is explained in the following with reference to FIG. 3.

Figure 3:
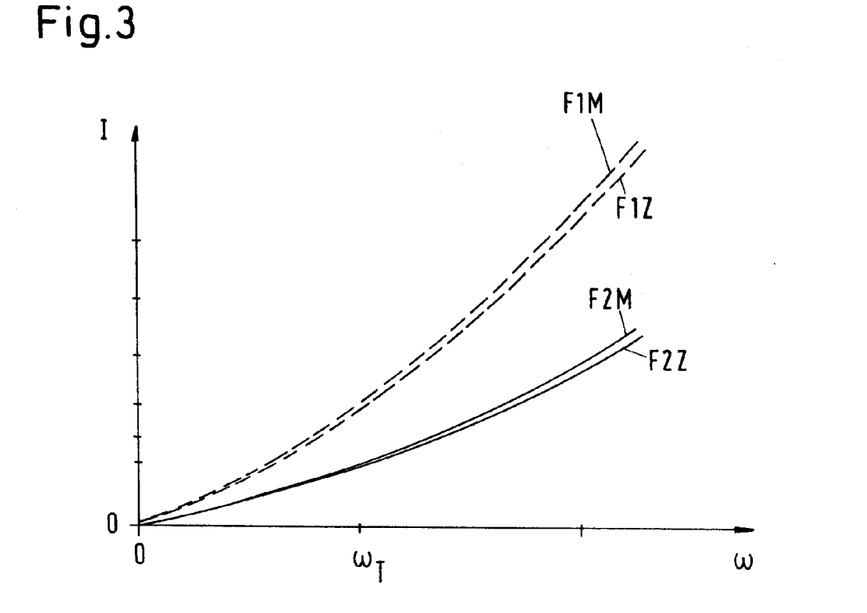
FIG. 3 is an illustration of the relationship between the motor current and the speed of rotation of the rotary pump for an embodiment of the method of the invention.

FIG. 3 shows an illustration of the motor current I in dependence on the speed of rotation ω of the pump for two fluids of different viscosity for an operating state of the rotary pump 1 in which its efficiency is very small. The dashed curves marked with F1M and F1Z relate to a fluid with high viscosity; the solid curves marked with F2M and F2Z relate to a fluid with lower viscosity. The upper of the two curves in each case, namely the curve marked with F1M or F2M, applies to the maximum flow (volume flow) which can be generated with the pump in this operating state; the lower of the two curves in each case, namely the curve marked with F1Z or F2Z, applies to the case that no flow at all is generated (volume flow has the constant value of zero). The large motor current I, which is explained in more detail below and which is entered on the ordinate, is directly a measure for the torque with which the rotor or the impeller wheel is driven. In the case of the preferred embodiment of the rotary pump as a bearing-free motor in particular, no mechanical bearing friction is present due to the magnetic support of the rotor so that the torque with which the rotor is driven agrees in a very good approximation to the torque transferred to the fluid.

Practically the whole torque and thus the mechanical power which the impeller wheel or the rotor transfers to the fluid is converted into friction losses in the liquid as a result of the very low efficiency at which the rotary pump 1 is operated in the operating state on which FIG. 3 is based. This can also be seen in FIG. 3 in particular from the fact that the curves F1M and F2M for maximum flow almost do not differ from the associated curves F1Z and F2Z for the flow zero. The torque of the impeller wheel is thus directly a measure for the viscosity, more precisely for the dynamic viscosity, of the fluid, because the mechanical power of the rotor is almost completely converted into friction losses of the liquid.

As already mentioned, the torque which the rotor transfers to the liquid essentially corresponds to the drive torque with which the rotor is driven, that is, except for mechanical friction losses. This applies in particular to magnetically supported rotors. The drive torque is in turn given by the motor current entered on the ordinate in FIG. 3 which drives the rotor. The motor current in this respect means the torque-forming portion of the current in the electrical drive, also known as the armature current. The armature current is a very good measure for the torque with which the rotor is driven, in particular in field-oriented three-phase motors and also in direct current motors.

Thus, in the operating range on which the illustration in FIG. 3 is based—that is, an operating range in which the rotary pump only works at a fraction of its maximum efficiency—there is a direct relationship between the motor current with which the pump is driven and the viscosity of the fluid. The dynamic viscosity of the fluid to be forwarded can thus be determined in a simple manner and online by a measurement of the motor current. A fixed test speed of rotation $\omega_T$ of the rotor is preferably set to determine the viscosity and the motor current is determined at this test speed of rotation $\omega_T$. The viscosity of the fluid is then known from the motor current thus determined, for example by a comparison with calibration measurements and/or on the basis of calculations. A particularly accurate determination of the viscosity can be realized by closing the outlet of the rotary pump, that is, by setting the constant volume flow to zero. The curves F1Z and F2Z in FIG. 3 correspond to such states in which the total mechanical power of the impeller wheel or of the rotor is converted into liquid friction.

This simple method for the determination of the viscosity of a fluid can naturally also be used for applications other than in conjunction with the forwarding of an adjustable, substantially constant volume flow.

The relationship illustrated in FIG. 2 between volume flow and speed of rotation is determined for different viscosities and stored in the form of typically electronic look-up tables or by means of mathematical approximations. If now a certain fluid is forwarded with the rotary pump 1, then (if its viscosity is not already known) first the viscosity of the fluid is determined at the given test speed of rotation $\omega_T$ (see FIG. 3). Subsequently, the unique relationship belonging to this viscosity between the volume flow and the speed of rotation (see FIG. 2) is chosen and the respectively desired constant volume flow of the fluid to be forwarded is set via the control of the speed of rotation of the rotor or of the impeller wheel.

A further advantageous measure consists of designing the flow resistance of the flow connection 4 (see FIG. 4) such that the pressure drop over the whole flow resistance, which is made up of the flow resistance of the flow connection 4 and the flow resistance of the dispensing apparatus 6 known as the load resistance, is substantially larger than possible pressure fluctuations at the dispensing apparatus 6. The total flow resistance of the flow connection 4 and of the dispensing apparatus 6 is advantageously selected such that its mean value is substantially larger than the fluctuations of the flow resistance during operation. "Substantially larger" is understood to mean "at least twice as large".

Changes in the load resistance or in the total flow resistance of the flow connection 4 and of the dispensing apparatus 6 can be caused, for example, by a filter slowly clogging up over time during operation.

Pressure fluctuations at the dispensing apparatus 6 can be caused, for example, by changes in the pumping head or of the flow resistance of the dispensing apparatus 6.

It is also advantageous if the total flow resistance is selected such that the pressure drop over the total flow resistance is substantially greater than pressure changes at the inlet to the rotary pump 1, which can be caused, for example, by an altered filling level of the reservoir or storage container 2.

In the arrangement of FIG. 4, the load resistance is substantially determined by the nozzle 61.

The measure of designing the flow connection 4 and the dispensing apparatus 6 as a large flow resistance which on average is substantially greater than its fluctuations has the advantage that the flow or volume flow of the fluid forwarded is independent of changes of the load resistance (as long as the change of the load resistance remains very much smaller than the mean total flow resistance). Variations can therefore occur at the hydraulic load resistance without the constant volume flow of the fluid 5 being changed thereby.

The flow resistance of the flow connection 4 can advantageously be changed. For instance, it can be matched to the fluid 5 to be forwarded. Furthermore, it can be ensured, by a change in the flow resistance of the flow connection 4, that the total flow resistance of the flow connection 4 and of the dispensing apparatus 6 is significantly larger on average than its fluctuations or that the pressure drop over the total flow resistance is substantially larger than pressure fluctuations at the dispensing apparatus 6.

One measure for changing the flow resistance of the flow connection 4 is indicated in FIG. 4. One or more loops 41 can be provided in the flow connection 4.

Figure 5:
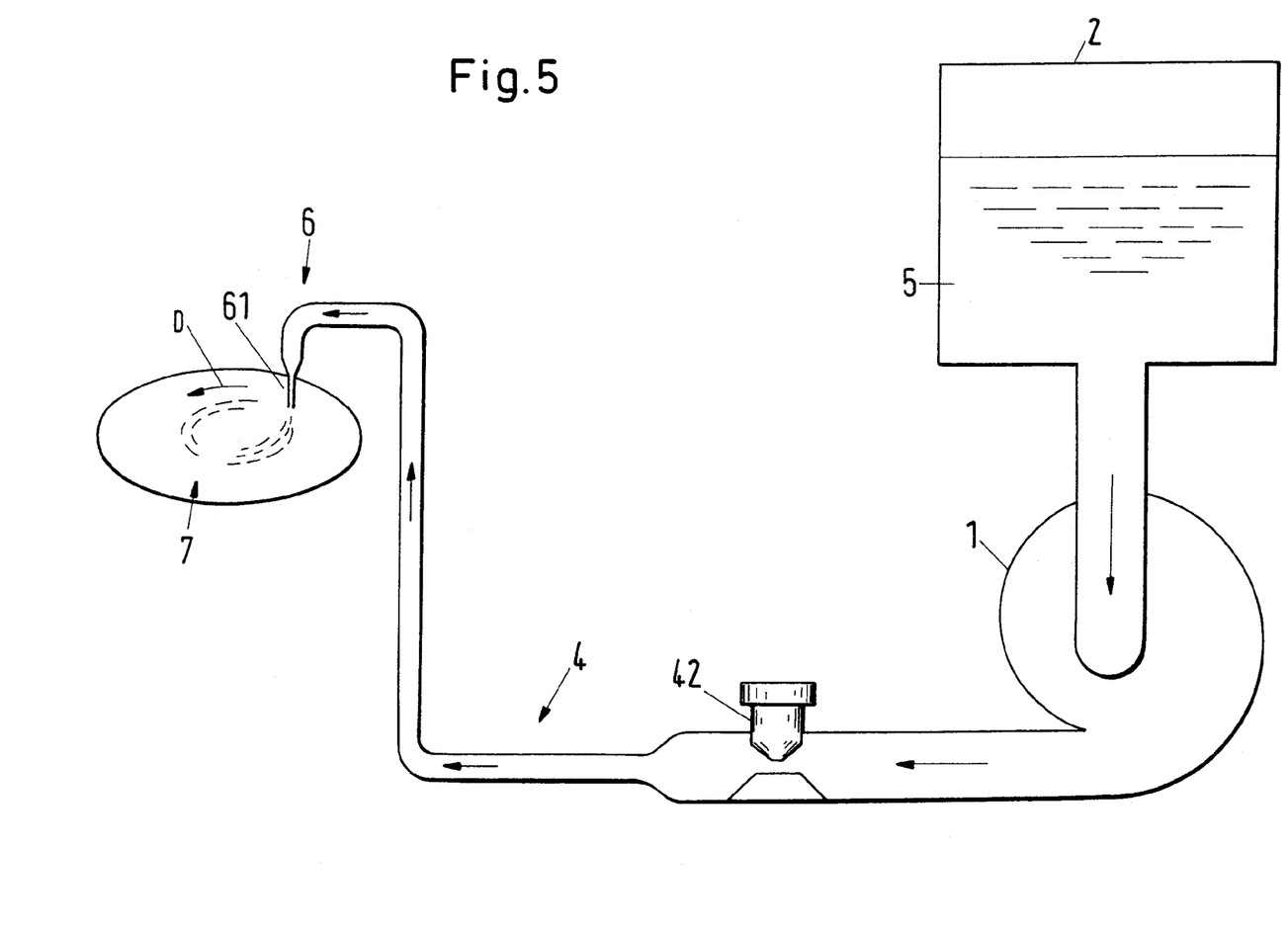
FIGS. 5–8 show variants of the arrangement shown in FIG. 4.

A further possibility to change the flow resistance of the flow connection 4 is shown in FIG. 5. Here, the flow connection 4 has an adjustable valve 42 with which the free flow cross-section and thus the flow resistance can be changed.

Figure 6:
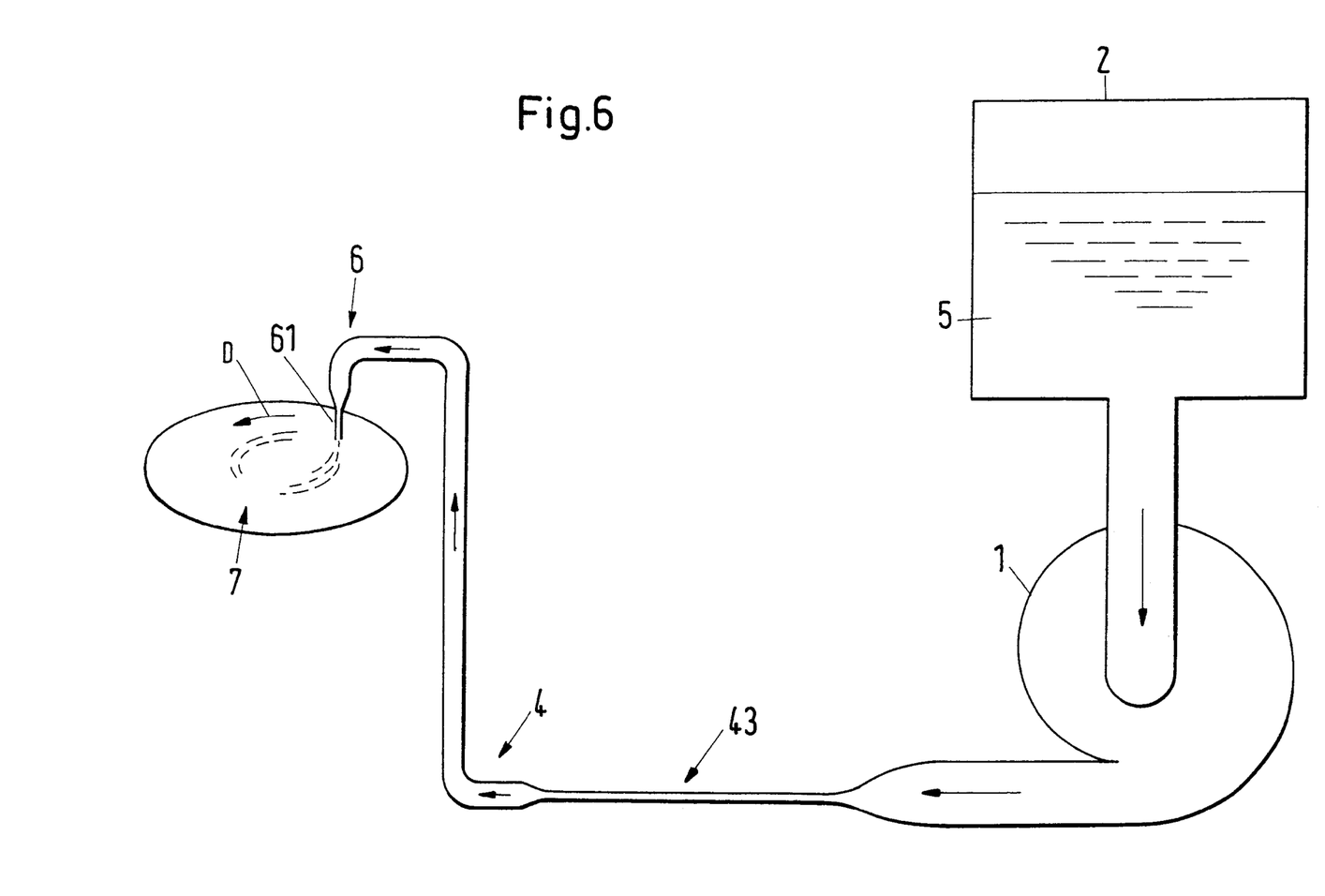

It is naturally also possible, as shown in FIG. 6, to change the flow resistance of the flow connection 4 by a restrictor line 43. The flow resistance can in this respect be adjusted by the length and/or the cross-section of the restrictor line 43.

For many applications, for example for the application of photosensitive resist to a semi-conductor, it is desirable for a predetermined volume of fluid to be forwarded. This can also be realized with the method of the invention. Since, in accordance with the invention, an adjustable, substantially constant volume flow is forwarded with the rotary pump 1, a predetermined quantity of fluid can be metered by using an ON/OFF valve which is, for example, time controlled.

Figure 7:
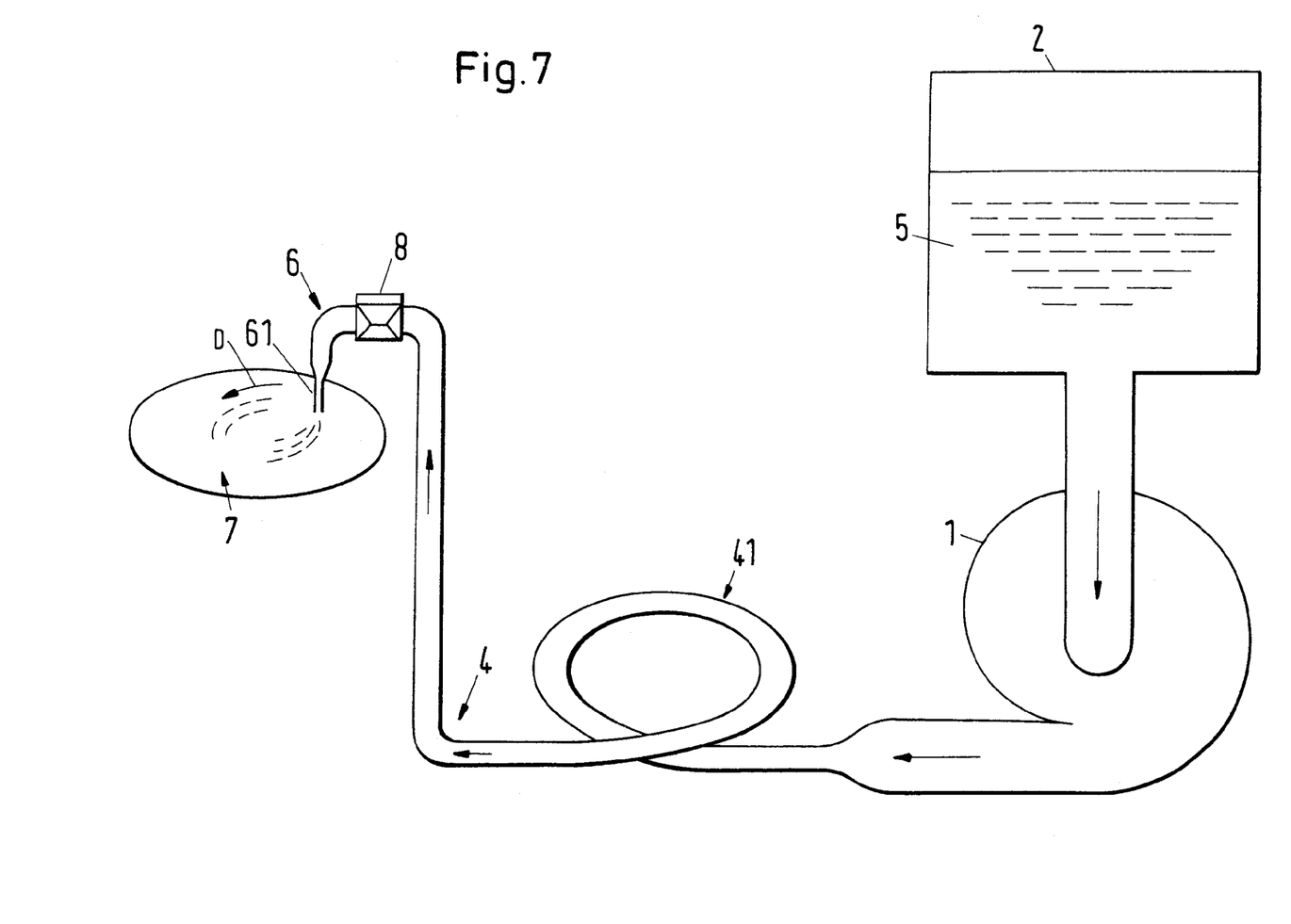

For this purpose, as shown in FIG. 7, an ON/OFF valve 8 or another shut-off apparatus is provided in the flow connection 4 or at the dispensing apparatus 6. The shut-off apparatus opens or closes the flow connection 4 to the dispensing apparatus 6. Since the rotary pump 1 forwards a volume flow which is constant time-wise, the quantity of the fluid applied to the wafer can be accurately metered via a time control of the ON/OFF valve 8. A particular advantage of the rotary pump 1 in this respect is that the rotary pump 1, unlike many known volumetric pumps, can also continue to run when the ON/OFF valve 8 closes the flow connection 4. It does not represent a problem for the rotary pump 1 to work against a closed outlet. The ON/OFF valve can naturally also be designed as a controllable valve or as a regulating valve.

Figure 8:
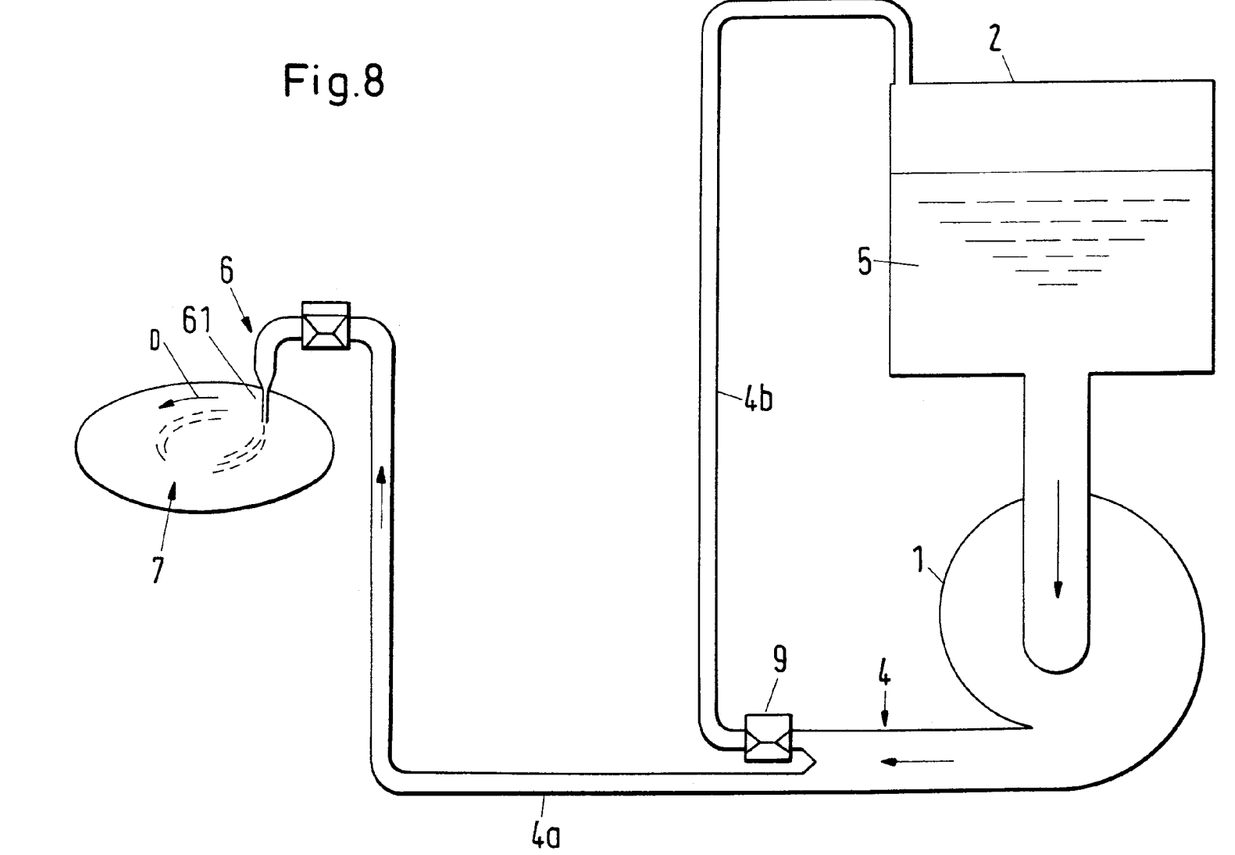

A further advantageous measure can be realized with the arrangement shown in FIG. 8. In this arrangement, the flow connection 4 forks into two branches 4a and 4b downstream of the rotary pump 1. The branch 4a leads in an analogous manner to that described above to the dispensing apparatus 6 via the ON/OFF valve 8. The second branch 4b leads back into the reservoir 2. A further valve 9, which can open and close the branch 4b, is provided in the second branch. If the valve 9 is open, then the fluid 5 is at least partly recirculated into the reservoir 2.

This measure is in particular advantageous for such fluids which tend to agglomeration, to phase separations, to precipitations or to deposits of particles, for example for suspensions, especially slurry solutions. The fluid 5 in the reservoir also keeps moving due to the recirculation so that a constant mixing takes place.

The valve 9 can, for example, be constantly open or partly open so that fluid 5 is constantly recirculated through the branch 4b. It is, however, for example, also possible to only open the valve 9 when the ON/OFF valve 8 is closed and vice versa. The valve 9 can naturally also be opened and closed without relationship to the ON/OFF valve 8.

A method is therefore proposed by the invention in which an adjustable, substantially constant volume flow of a fluid to be generated is generated with a rotary pump, for example with a centrifugal pump. It is not necessary for this purpose to regulate the throughflow of the rotary pump with the aid of corresponding sensors, but rather the desired volume flow is set directly by a control of the speed of rotation (that is, without an additional control).

The method of the invention is naturally not limited to the application described here, namely to the transportation of a slurry suspension or to CMP processes. It is also generally suitable, among other things, for the transportation of suspensions, emulsions, paints, foods (e.g. juices or concentrates) or, for example, for the coating of films and belts.

In accordance with the invention, a pump apparatus is furthermore provided for the generation of an adjustable, substantially constant volume flow of slurry in a chemical-mechanical polishing process (CMP) or for the generation of an adjustable, substantially constant volume flow of a coating fluid, for example photosensitive resist, which pump apparatus is characterized in that it is designed as a rotary pump (1).

What is claimed is:

1. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein the fluid is forwarded through the flow connection to a dispensing apparatus, the total flow resistance of the flow connection and of the dispensing apparatus being selected such that its mean value is substantially larger than the fluctuations during operation.

2. A method in accordance with claim 1, wherein the flow resistance of the flow connection can be changed and is matched to the fluid to be forwarded.

3. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein the flow resistance of the flow connection can be changed and is matched to the fluid to be forwarded.

4. A method in accordance with claim 3, wherein the rotary pump is operated at at most twenty percent of its maximum efficiency.

5. A method in accordance with claim 3, wherein the fluid is forwarded through the flow connection to a dispensing apparatus, with the total flow resistance of the flow connection and of the dispensing apparatus being selected such that its mean value is substantially larger than the fluctuations during operation.

6. A method in accordance with claim 3, and wherein the fluid is forwarded through the flow connection to a dispensing apparatus, the total flow resistance of the flow connection and of the dispensing apparatus being selected such that the pressure drop over the total flow resistance is substantially larger than the pressure fluctuations at the dispensing apparatus.

7. A method in accordance with claim 3, wherein the fluid is forwarded through the flow connection to a dispensing apparatus, with the total flow resistance of the flow connection and of the dispensing apparatus being selected such that the pressure drop over the total flow resistance is substantially larger than pressure changes at the inlet of the rotary pump.

8. A method in accordance with claim 3, wherein the volume flow is only set by the speed of rotation of the rotary pump.

9. A method in accordance with claim 3, wherein an ON/OFF valve is provided in the flow connection or at a dispensing apparatus.

10. A method in accordance with claim 3, wherein the fluid is at least partly recirculated into the reservoir.

11. A method in accordance with claim 3, wherein the rotary pump has an integral rotor and is designed as a bearing-free motor.

12. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein the fluid is forwarded through the flow connection to a dispensing apparatus, the total flow resistance of the flow connection and of the dispensing apparatus being selected such that its mean value is substantially larger than the fluctuations during operation, and wherein the fluid is forwarded through the flow connection to a dispensing apparatus, with the total flow resistance of the flow connection and of the dispensing apparatus being selected such that the pressure drop over the total flow resistance is substantially larger than the pressure fluctuations at the dispensing apparatus.

13. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein the fluid is forwarded through the flow connection to a dispensing apparatus, with the total flow resistance of the flow connection and of the dispensing apparatus being selected such that the pressure drop over the total flow resistance is substantially larger than pressure changes at the inlet of the rotary pump.

14. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein an ON/OFF valve is provided in the flow connection or at a dispensing apparatus.

15. A method for the generation of an adjustable, substantially constant volume flow of a fluid by means of a pump apparatus in which the fluid is forwarded by the pump apparatus from a reservoir into a flow connection, wherein a rotary pump is used as the pump apparatus and the rotary pump is operated at an efficiency which is less than half a maximum efficiency of the rotary pump, and wherein the fluid is at least partly recirculated into the reservoir.

16. A method of supplying an accurately metered quantity of a liquid from a reservoir to a flow connection comprising providing a rotary pump for pumping the liquid, and metering the liquid discharged by the pump by operating the pump for a sustained period of time at an efficiency which is less than half a maximum efficiency of the rotary pump.

17. A method according to claim 16 including operating the pump at an efficiency which is no more than about twenty percent of the maximum efficiency of the rotary pump.

18. A method according to claim 16 including varying a quantity of liquid discharged by the pump by changing at least one of a rotational speed of the pump and a flow resistance acting at a discharge end of the pump.

19. A method of dispensing metered quantities of a liquid discharged by a rotary pump having a maximum efficiency comprising operating the pump at a reduced efficiency of less than about half the maximum efficiency of the pump, and flowing the fluid through the pump while the pump operates at the reduced efficiency for a sustained period of time, whereby the efficiency of the rotary pump is such that a volumetric liquid flow through the pump is substantially directly related to the rotational speed of the pump.

20. A method of supplying metered quantities of an abrasive slurry in a chemical-mechanical-polishing process on semiconductor surfaces comprising providing a rotary pump having a maximum efficiency, operating the pump at a reduced efficiency of less than about half the maximum efficiency of the pump, and flowing the slurry through the pump while the pump operates at the reduced efficiency, whereby the efficiency of the rotary pump is such that a volumetric slurry flow through the pump is substantially directly related to the rotational speed of the pump and thereby accurately metered.

21. A chemical-mechanical-polishing process for a semiconductor wafer comprising rotary polishing a surface of the wafer, and supplying metered amounts of a slurry including abrasives by providing a rotary pump, having a maximum efficiency, operating the pump at a reduced efficiency of less than about half the maximum efficiency of the pump, and flowing the slurry through the pump while the pump operates at the reduced efficiency, whereby the efficiency of the rotary pump is such that a volumetric slurry flow through the pump is substantially directly related to the rotational speed of the pump and thereby accurately metered.

* * * * *